US009949712B1

(12) United States Patent
Millard et al.

(10) Patent No.: US 9,949,712 B1
(45) Date of Patent: Apr. 24, 2018

(54) APPARATUS AND METHOD FOR MEASURING THE SOUND TRANSMISSION CHARACTERISTICS OF THE CENTRAL NERVOUS SYSTEM VOLUME OF HUMANS

(71) Applicants: John William Millard, Wichita, KS (US); Curtis Lane Prichard, Springfield, MO (US)

(72) Inventors: John William Millard, Wichita, KS (US); Curtis Lane Prichard, Springfield, MO (US)

(*) Notice: Subject to any disclaimer, the term of this patent is extended or adjusted under 35 U.S.C. 154(b) by 162 days.

(21) Appl. No.: 14/479,819

(22) Filed: Sep. 8, 2014

Related U.S. Application Data

(60) Provisional application No. 61/874,600, filed on Sep. 6, 2013.

(51) Int. Cl.
*A61B 5/00* (2006.01)
*A61B 7/00* (2006.01)
*A61B 5/145* (2006.01)
*A61B 5/03* (2006.01)

(52) U.S. Cl.
CPC ............ *A61B 7/006* (2013.01); *A61B 5/032* (2013.01); *A61B 5/14507* (2013.01)

(58) Field of Classification Search
CPC .... A61B 5/7279; A61B 5/7282; A61B 5/7405
See application file for complete search history.

(56) References Cited

U.S. PATENT DOCUMENTS

| 3,605,021 A | * | 9/1971 | Mychalowych | ........ H04L 27/10 375/223 |
| 3,872,443 A | * | 3/1975 | Ott | ........................ A61B 5/1107 181/126 |
| 4,048,986 A | * | 9/1977 | Ott | ........................ A61B 5/117 340/5.82 |
| 4,361,154 A | * | 11/1982 | Pratt, Jr. | ............... A01K 29/005 600/437 |
| 4,530,360 A | * | 7/1985 | Duarte | ............... A61H 23/0245 607/51 |
| 4,754,763 A | * | 7/1988 | Doemland | ........... A61B 5/4504 600/552 |

(Continued)

OTHER PUBLICATIONS

M. Akay and W. Welkowitz, Acoustical Detection of Coronary Occlusions Using Neural Networks, Journal of Biomed. Eng., 1993, vol. 15, November.

*Primary Examiner* — Michael C Stout
(74) *Attorney, Agent, or Firm* — Robert Blinn

(57) ABSTRACT

An apparatus for detecting the presence of pathogens in cerebrospinal fluid (CSF) within the central nervous system (CNS) includes a digital computer, a speaker unit and a microphone unit. The digital computer is programmed with generally available software which is capable of generating a spectrum of sound and receiving microphone data. The software is able to receive microphone signals and represent resulting data in graphical form showing sound intensity in dB as a function of frequency in kHz. An operator places the speaker and the microphone on the subject's body so that sound travels through at least a portion of the CNS, runs the software, and collects the resulting sound propagation data. If the propagation of sound through the CNS is indicative of altered CSF or CNS, then a disease state is suspected.

4 Claims, 7 Drawing Sheets

(56) References Cited

U.S. PATENT DOCUMENTS

| | | | | |
|---|---|---|---|---|
| 5,024,239 | A * | 6/1991 | Rosenstein | A61B 5/0051 600/552 |
| 5,239,997 | A * | 8/1993 | Guarino | A61B 8/08 600/587 |
| 5,402,781 | A * | 4/1995 | Dimarogonas | A61B 5/0051 600/407 |
| 5,603,325 | A * | 2/1997 | Mazess | A61B 8/0875 600/442 |
| 5,836,876 | A * | 11/1998 | Dimarogonas | A61B 5/0051 600/407 |
| 5,853,005 | A * | 12/1998 | Scanlon | A61B 5/113 29/235.5 |
| 6,082,367 | A * | 7/2000 | Greeninger | A61N 1/37258 128/899 |
| 6,336,045 | B1 * | 1/2002 | Brooks | A61B 5/053 600/407 |
| 6,754,472 | B1 * | 6/2004 | Williams | H04Q 9/04 455/100 |
| 7,664,277 | B2 * | 2/2010 | Abolfathi | A61C 5/00 381/151 |
| 8,731,205 | B2 * | 5/2014 | Parker | H04R 25/606 381/59 |
| 8,870,791 | B2 * | 10/2014 | Sabatino | A61B 7/00 381/67 |
| 8,882,683 | B2 * | 11/2014 | Horii | A61B 5/087 600/586 |
| 8,945,133 | B2 * | 2/2015 | Stein | A61B 5/107 600/424 |
| 2002/0169378 | A1 * | 11/2002 | Mo | A61B 8/00 600/437 |
| 2002/0183642 | A1 * | 12/2002 | Murphy | A61B 5/061 600/532 |
| 2004/0037428 | A1 * | 2/2004 | Keller | A61B 5/121 381/60 |
| 2008/0262350 | A1 | 10/2008 | Unger | |
| 2009/0177097 | A1 * | 7/2009 | Ma | A63B 71/0686 600/500 |
| 2010/0049082 | A1 | 2/2010 | Hu et al. | |
| 2010/0256529 | A1 * | 10/2010 | Grasing | A61B 7/04 600/586 |
| 2010/0305437 | A1 | 12/2010 | Liebschner et al. | |
| 2011/0129097 | A1 * | 6/2011 | Andrea | H04R 3/005 381/71.6 |
| 2012/0190303 | A1 * | 7/2012 | Wong | A61B 7/02 455/41.2 |
| 2013/0018240 | A1 * | 1/2013 | McCoy | A61B 5/05 600/323 |
| 2013/0278396 | A1 * | 10/2013 | Kimmel | G08C 17/02 340/12.5 |

* cited by examiner

APPARATUS AND METHOD FOR MEASURING THE SOUND TRANSMISSION CHARACTERISTICS OF THE CENTRAL NERVOUS SYSTEM VOLUME OF HUMANS

CROSS REFERENCES TO RELATED APPLICATIONS

This application claims the benefit of U.S. Provisional Patent Application 61/874,600 filed on Sep. 6, 2013, which is incorporated herein by reference.

FIELD

This invention relates to an apparatus and method for measuring the sound transmission characteristics of a spinal column with the objective of detecting or ruling out the presence of spinal column fluid contaminants, or in combination with, abnormal concentrations of normal constituents or other abnormalities in the volume occupied by the human central nervous system which might indicate a disease state.

BACKGROUND

A number of disease states result in some degree of contamination of cerebrospinal fluid (CSF). The skilled reader will recall that the brain and the spinal chord reside within the cranium and the spinal column respectively. Both the brain and the spinal column of the human central nervous system (CNS) are exquisitely delicate and therefore are surrounded by cerebrospinal fluid (CSF) in both the cranium and the spinal column. Further, the brain itself includes passages and sinuses which are also filled with CSF. The CSF of a normal, healthy patient is typically very pure and typically free of blood cells, foreign particles, pathogens, bacteria or any other form of contaminant. Several disease states may disrupt or compromise the purity of CSF. Two examples include meningitis and hemorrhagic stroke.

Meningitis is an inflammation of the membranes surrounding the brain and the spinal cord which are collectively known as the meninges. Frequently, such an inflammation is caused by a bacterial infection. Accordingly, in common parlance, the term "meningitis" is often used as a general term to refer to such an infection. As such, meningitis can be indicative of an extremely dangerous and potentially fatal infection. For this reason, a meningitis infection is considered to be an emergency condition. The early detection and treatment of meningitis is of the utmost importance if there is to be a positive outcome for a patient. The present standard of care in the diagnosis of meningitis includes the insertion of a needle into the spinal column between two vertebrae and the extraction of CSF. The act of inserting a needle for extracting CSF is also referred to as a "lumbar puncture". Once CSF is extracted, it is tested using agar plate testing to identify an infecting agent. This process can take up to 72 hours and the test will yield a negative result unless there is a significant presence of an infecting organism. Once a diagnosis is made, rapid and aggressive treatment is vital for improving the patient's outcome. Any delay in the inception of treatment increases the risk of neurological complications including: impaired mental status, increased intra-cranial pressure, cerebral edema, seizures, cerebrovascular abnormalities, hearing loss, intellectual impairment, and death. A method that offers an immediate diagnosis of meningitis would improve patient outcomes and would also provide a contraindication in performing a risky lumbar puncture for the extraction of CSF. The complications that can occur as a result of lumbar punctures are not trivial. They include post-lumbar puncture headache which occurs in up to 40% of patients, short or long term back discomfort or pain, bleeding into epidural space, brainstem herniation, paraplegia, infection, and even though very rare, death.

At an early stage, meningitis resembles influenza, making initial diagnosis difficult without the classical symptom of nuchal rigidity (a stiff neck). An early missed diagnosis results in the loss of the early critical treatment period. What is needed is a non-invasive, reliable test for determining if a patient has meningitis.

A hemorrhagic stroke is a condition wherein an artery associated with supplying blood to the brain ruptures. A hemorrhagic stroke can occur when an artery supplying blood to the brain harbors an aneurysm. Such ruptures very often result in blood being released into the CSF. This in turn causes the CSF to be contaminated with blood cells and other blood constituents. A significant concern in the early diagnosis of a stroke is to distinguish a hemorrhagic stroke from an ischemic stroke. Recall that ischemic strokes result from a blood clot in the brain. Ischemic strokes are generally not accompanied by the release of blood into the CSF. The importance of distinguishing between hemorrhagic strokes and ischemic strokes is related to the initial therapy often administered to ischemic stroke patients. Such initial therapy often includes the administration of drugs which are directed toward breaking up blood clots. The administration of such drugs in the case of a hemorrhagic stroke would most likely aggravate the intra-cranial bleeding and harm the patient. Accordingly, what is needed is a means for quickly distinguishing between an ischemic and a hemorrhagic stroke.

SUMMARY

The above stated needs are addressed by an apparatus and method that provides a non-invasive means for detecting contaminants in CSF which is often indicative of a disease state. When meningitis is present, bacteria are present in the spinal fluid. When a hemorrhagic stroke has occurred, very likely, blood contaminates the CSF. Normally, CSF is essentially sterile and free from any contaminants. Accordingly, a non-invasive test which can detect a pathological contaminant in the CSF can be used to either diagnose meningitis or rule it out or might be used to diagnose a hemorrhagic stroke or rule it out. In this discussion we will use the term pathological contaminant to indicate any contaminant that might be present in the CSF which is associated with a disease process. Such disease processes might include strokes which lead to blood cells contaminating the CSF or various types of bacterial or viral infections, including meningitis, or even contaminants released into the CSF as a result of neck or back pain via inflammatory mediators. Contaminants include endogenous constituents in abnormal amounts. Pressure changes in CSF are captured for diagnosis purposes by the apparatus as well and are included under the term "diagnosis".

The present apparatus and method is employed to conduct such a test by transmitting sound through a portion of the patient's spinal column and measuring how readily sound is transmitted across a spectrum of frequencies. The applicants have learned that an elongated tube filled with artificial CSF has measurably different sound transmission properties than the same tube filled with artificial CSF having even small concentrations of micro-beads which have physical characteristics very similar to those of bacteria or blood cells. In particular, the applicant's constructed a simulated, artificial spinal column and tested it when containing sterile fluid and fluid contaminated with approximately 100 particles per mL of 3 μm diameter polystyrene beads. When the tests were conducted, the applicants determined the sound transmission characteristics of the contaminated artificial CSF differed measurably from that of the sterile artificial CSF. By distinguishing between an uncontaminated normal sound transmission response and a contaminated abnormal sound transmission response, the apparatus may be used to detect the presence of pathological contaminants, such as blood or bacteria.

The apparatus includes a speaker and a microphone which are connected to a digital computer (hereafter "computer") such as a laptop computer. Those skilled in the art will appreciate that a desktop computer may be used or perhaps even a smart phone could be programmed with an application that would execute the steps of the method. In this example, SpectraPLUS-SC™ software by Pioneer Hill Software LLC which may be obtained at www.spectraplus.com was used to generate the sound, receive the sound and capture and analyze the results. A technician conducts the method by (a) activating the computer and the testing software loaded on the computer, (b) placing the speaker and the microphone so that they are spaced apart on the spine of a patient and (c) running the test software. When the technician runs the software, the software executes the following steps: (a) an ascending or descending series of tones or both is generated in the speaker and (b) a corresponding detection of sound is collected by the microphone and stored in a file in the computer. The preferred software noted above collects the data and generates a graph which plots the degree of sound transmission in decibels (db) as a function of frequency. The applicants have found for adult subjects tested, when test subjects are exposed to a range of sounds between 0.5 kHz and 1.5 kHz, harmonic resonance frequency zones which are typically less than 0.5 kHz in width occur at approximately 3 kHz and between 10 kHz and 15 kHz. Apparently, typically, the zones of harmonic resonance represent frequency ranges in which the CSF volume produce harmonics or in which such harmonics are readily transmitted in normal human CSF. Conversely, the applicants believe that when patients with meningitis (or any other bacterial infection of the spinal fluid) are tested, or with blood contaminating the CSF (as is the case with an hemorrhagic stoke) harmonic sound in these frequency ranges will not propagate as readily or will propagate differently in a way that will be indicative of contaminated CSF. Accordingly, it should be possible to use this apparatus and method to non-invasively either detect or rule out the presence of contaminants in the CSF.

DETAILED DESCRIPTION

Figure 1:
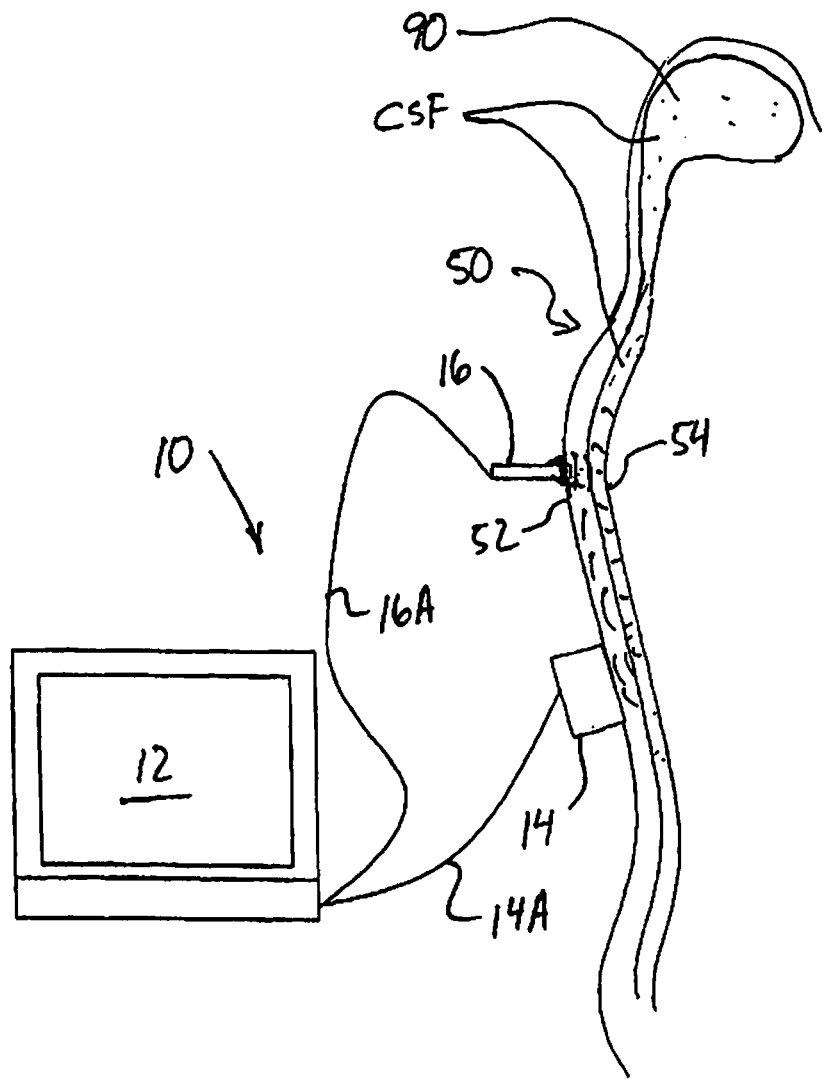
FIG. 1 is a diagram showing the sound transmission diagnostic apparatus positioned for measuring the sound transmission characteristics of a human spinal column.

Referring to the drawings, FIG. 1 illustrates a sound transmission diagnostic apparatus 10 which is adapted in this example for detecting the presence of pathogenic contaminants in cerebrospinal fluid (CSF) within the CNS volume. Such pathogenic contaminants may include bacteria in the case of meningitis, blood in the case of a hemorrhagic stroke or even histamines or other contaminants that might be released into the CSF as a result of neck or back pain. The applicants contemplate that other factors might alter the sound transmission properties of the CNS volume such as bulging or misplaced inter-vertebral discs which might accompany chronic back or neck pain. As can be seen in FIG. 1, diagnostic apparatus 10 includes a computer 12 a speaker 14 and a microphone 16. In this example, a speaker lead 14A connects between the speaker interface of computer 12 and speaker 14. In this example, the speaker is an X-MINI™ capsule speaker manufactured by XMI PTE, Ltd. that is surrounded by a cylindrical ½ inch thick foam rubber sound insulating shroud to improve contact with a subject's spinal column and improve the isolation of the sound from ambient sound. Preferably, the sound generated by this speaker during data collection is maintained near the maximum volume of the speaker. In this example, the microphone may be a typical USB desktop microphone for a portable or notebook computer that is capable of detecting sounds between 20 Hz and 20kHz. A microphone lead 16A connects between the microphone interface of computer 12 and microphone 16. In this example, computer 12 is loaded with SpectraPLUS-SC which can be obtained from Pioneer Hill Software LLC and computer 12 is fully capable of running that software. As can be seen in FIG. 1, speaker 16 is located approximately on the lumbar vertebral region and microphone 14 is located approximately on the cervical vertebral region. However, the applicants have found that these locations may be reversed and it will still be possible to obtain useful readings. The remaining figures, as will be discussed below, provide graphs that show the signal response that occurs when sound is conducted as described below.

Figure 2:
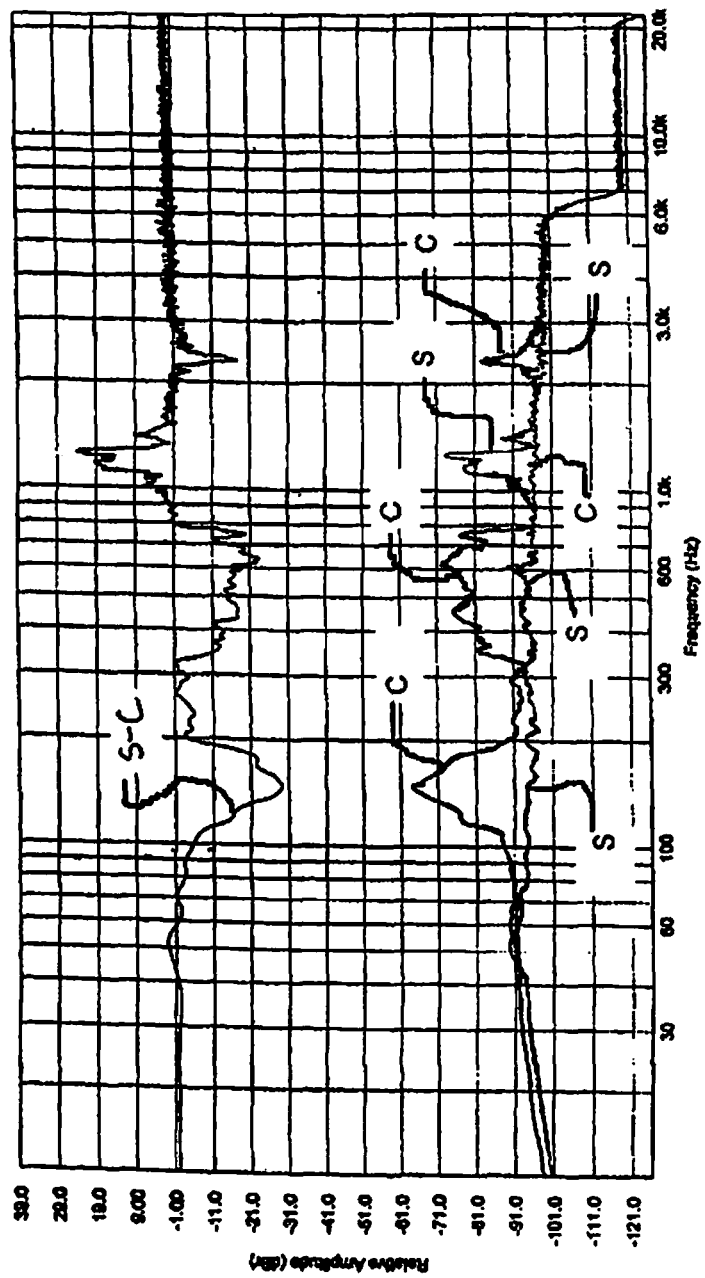
FIG. 2 is a graph showing the varying transmission of sound as a function of frequency in Hz in a simulated artificial spinal column containing sterile artificial spinal fluid versus a simulated artificial spinal column contaminated with micro-beads selected to simulate bacteria as well as the difference between the sterile and contaminated artificial spinal column data.

FIG. 2 shows the signal response of an artificial, simulated spinal column that is modeled by a plastic tube filled with artificial spinal fluid. Artificial spinal fluid may be obtained from Harvard Apparatus. Harvard Apparatus refers to this material as "Artificial CSF Perfusion Fluid". The trace marked C indicates the signal response that occurs when a contaminant is present. In this example, the contaminant is polystyrene latex beads having an average diameter of 3 μm (which is comparable to the average size of bacteria which range in size between 0.2 and 5 microns). These beads consist of 69% water, 30% polymer and less than 2% surfactant and inorganic salts. The concentration of the beads was approximately 100 particles per mL. It is believed that this contaminant closely resembles the presence of a similar concentration of bacteria or other contaminants such as blood cells and other blood continuants. Those skilled in the art will quickly recognize that a concentration of 100 bacteria per mL would be consistent with a very low level of infection. As can be seen in FIG. 2, the signal response of the contaminated specimen differs markedly from the signal response of the otherwise identical sterile specimen. The trace marked S-C in FIG. 2 shows the differences between the sterile and contaminated traces. FIG. 2 demonstrates it is possible to detect the presence of a contaminant that closely models bacteria, even in small concentrations, in a cylinder of fluid which is configured to simulate a spinal column.

Figure 3:
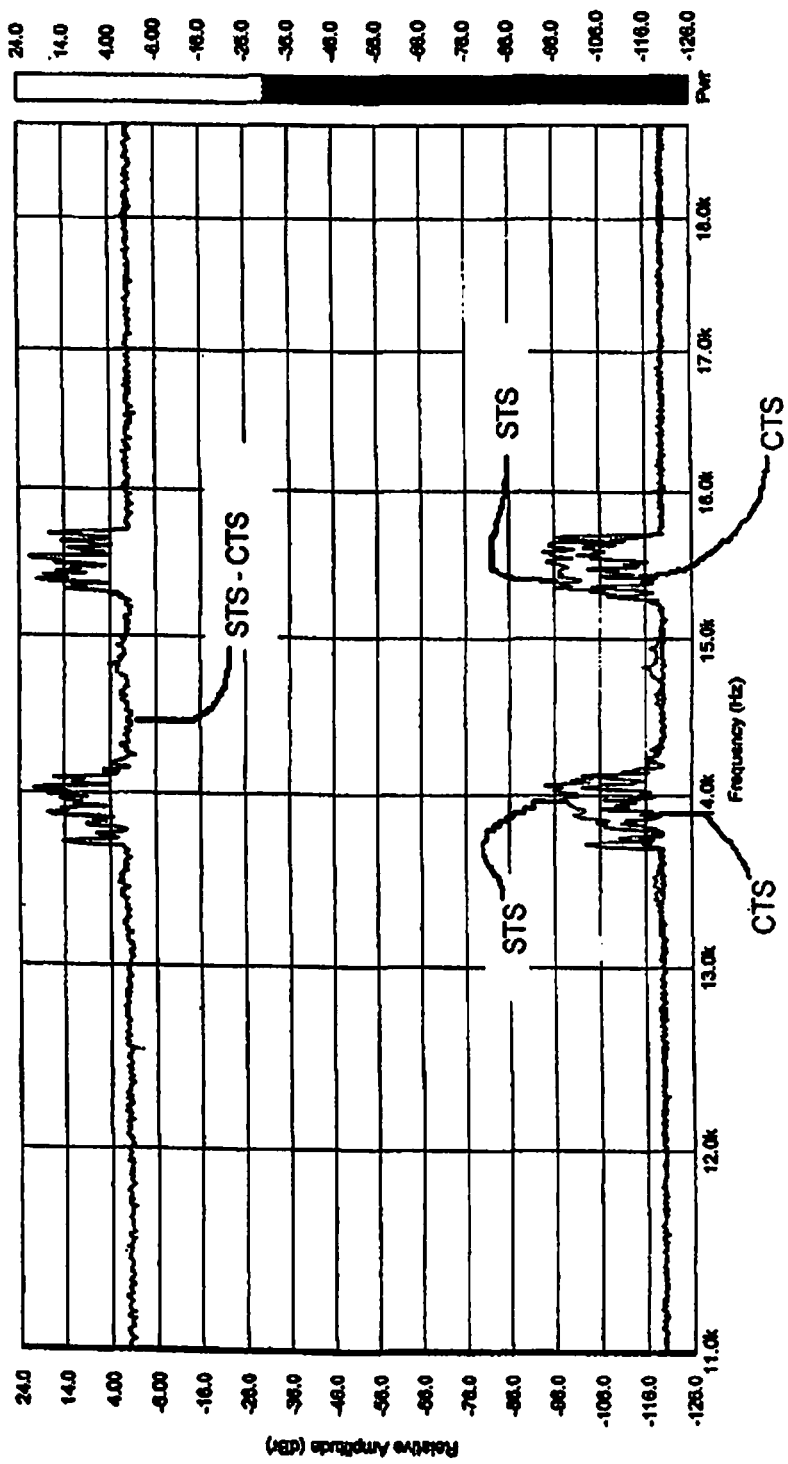
FIG. 3 is a graph showing the transmission of sound as a function of frequency in Hz when sound is propagated between the chest and spine and between two locations spaced apart on the spine in a normal male subject who is presenting no symptoms of meningitis.

FIG. 3 shows the sound propagation characteristics of a normal male test subject. Three traces are present in this figure. A first trace marked CTS (chest-to-spine) shows the sound propagation response that occurs when speaker 14 is placed on the sternum (chest) and microphone 16 is placed proximate to spinal column 54 (directly on the spinal column). A second trace marked STS shows sound propagation response that occurs when speaker 14 is placed proximate to spinal column 54 in the lumbar region and microphone 16 is spaced away from speaker 14 and also placed proximate spinal column 54 in the cervical region_as shown in FIG. 1. In this example, the speaker and the microphone are placed preferably directly on the skin surface 52 of test subject 50 as close as possible to the spinal column 54 and are preferably spaced apart preferably by at least 5 inches and preferably by not more than 15 inches and most preferably in the lumbar and cervical regions respectively as noted above. In this example the speaker generates sound at frequencies between 0.5 kHz and 1.5 kHz.

The applicants believe that apparatus 10 is useful for measuring the acoustic characteristics of the central nervous system (CNS) volume which, as the skilled reader will recall, is the volume occupied by the human central nervous system. The volume occupied the human CNS should be understood as including the cavity defined by the cranium and the spinal cavity defined by the spinal column. As the skilled reader will also recall, the CNS is continuous and is occupied by the brain which includes channels and sinuses (which are also filled with CSF) and which, in the spinal cavity, is also occupied by the spinal column. The skilled reader will further recall that the brain and the spinal chord are bathed in CSF. As noted above the CNS volume is also enclosed by a continuous set of membranes which are collectively known as the meninges.

While most of the figures present wide output ranges which extend between 20 Hz and 20 kHz on a logarithmic scale, FIG. 3 employs a linear scale and the output range is limited to a range between 11 kHz and 18 kHz. The STS trace of FIG. 3 shows there are significant resonances in the central nervous system (CNS) volume centered at approximately 14 kHz and 15.5 kHz. This may be occurring because sound propagates more readily through the CNS volume near these frequencies or perhaps because harmonics are more easily generated at these frequencies or both. Further, since the sound input is between 0.5k Hz and 1.5k Hz, the spiked areas of increased amplitude centered at approximately 14 kHz and 15.5 kHz in FIG. 3 appear to represent harmonics of the initial input. The applicants believe that the increased amplitude areas at approximately 14 kHz and 15.5 kHz are zones in which harmonics of the input sounds resonate because the input sound does not extend above 1.5 kHz which is a frequency which is nearly an order of magnitude below the spiked zones. As can be seen in FIG. 3, these spiked areas of increased amplitude extend roughly 0.5 kHZ around both of these locations. The applicants suspect that since the CTS (chest-to-spine) trace shown in FIG. 3 presents a similar but muted pattern, even those signal responses, which are also centered at 14 kHz and 15.5 kHz, may be caused by sound resonating in at least some portion of the CNS volume. The applicants caution the skilled reader that the 14 kHz and 15.5 kHz values given above may be specific to the test subject and may vary depending on the physical size of the test subject or may vary depending on other factors. Since the test subject was normal and presumably free of infection (and therefore having sterile spinal column fluid), the applicants believe a distortion of this normal harmonic resonance pattern shown by the STS trace in FIG. 3 will occur when a patient who is infected with meningitis is tested using the above described method. Distortions of these harmonic zones may also be evident if the test subject is presenting other disease states such as stroke or even chronic neck or back pain or other disease states that might alter the CSF. It is these distortions which will provide a means for detecting the presence of abnormal alterations of the CSF. While the harmonic resonant frequencies may vary slightly between test subjects, the applicants believe, the change in response caused by the presence of abnormalities in the fluid of the CNS volume will be distinctive and recognizable as was the case with the simulated spinal column as noted in the discussion of FIG. 2 immediately above. Conversely, the absence of any significant variance from a normal response may allow a medical practitioner to rule out the presence of various disease states.

Figure 4:
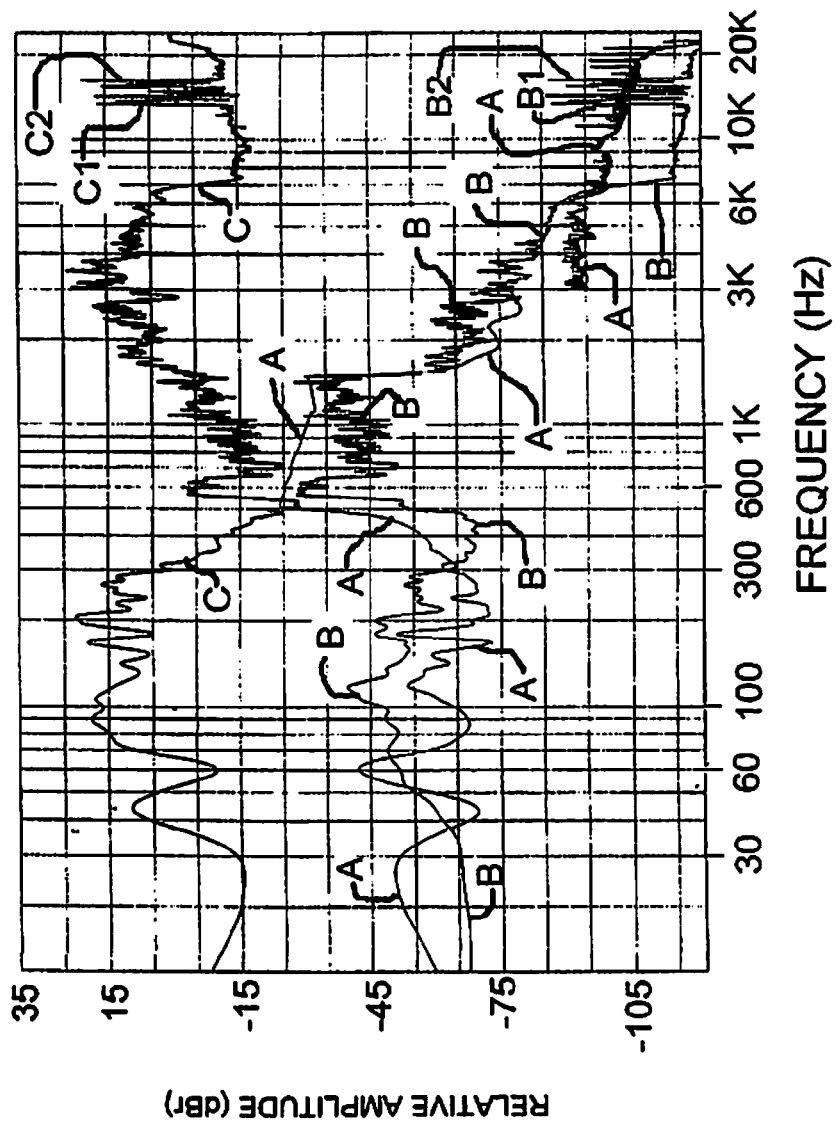
FIG. 4 is a graph showing the transmission of sound as a function of frequency in Hz when sound is propagated. Trace A is a control with the apparatus operating in a sound isolated chamber with no patient. Trace B shows the frequency response when a frequency generator ranges between 500 Hz and 1500 Hz and a microphone detects sound between 1 kHz and 20 kHz and the speaker is placed approximately on the lumbar vertebral region of the back and the microphone is placed approximately on the cervical vertebral region of the neck on a normal subject. Trace C is the difference between trace A and trace B.
Figure 5:
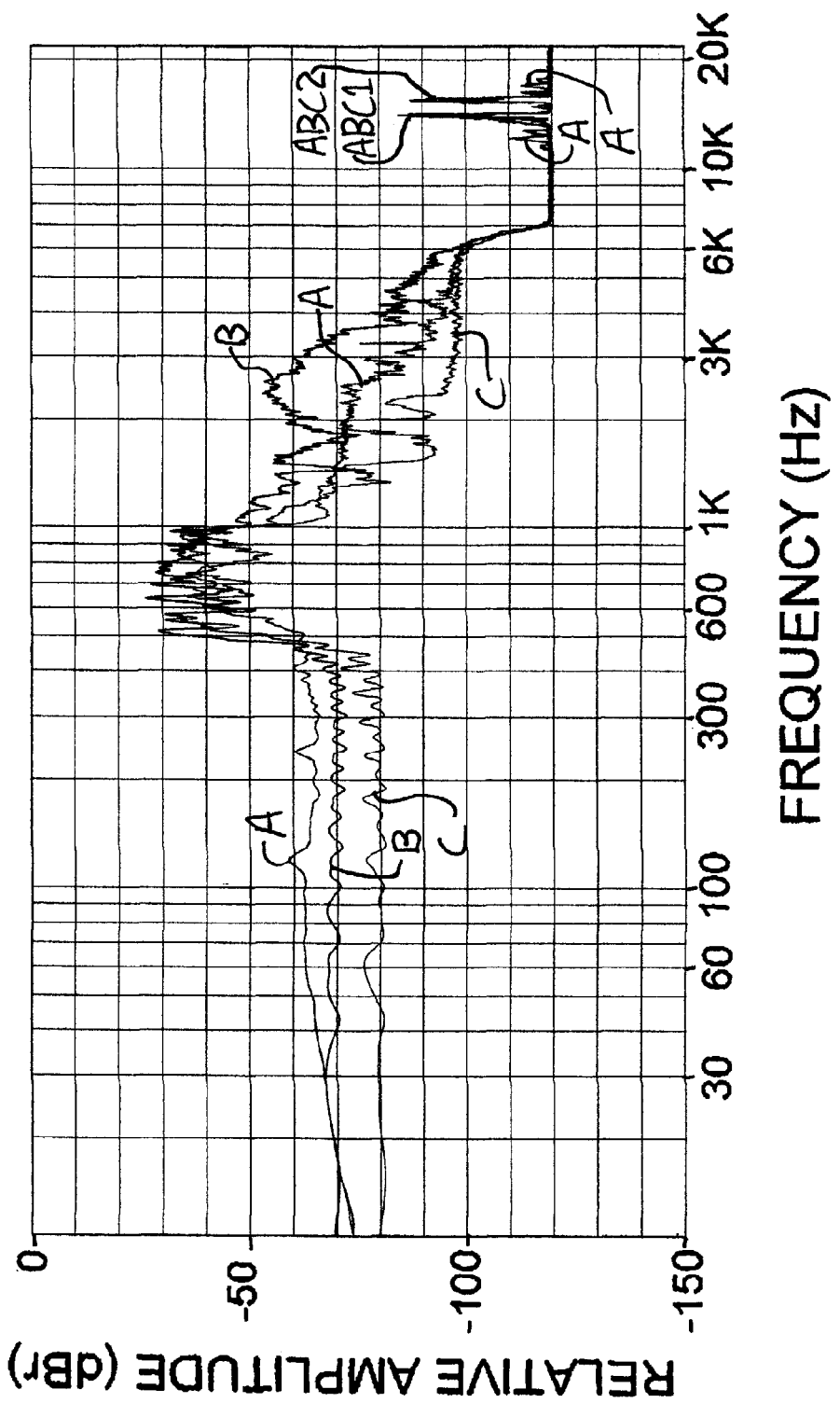
FIG. 5 is a graph showing the transmission of sound as a function of frequency in Hz when for three normal individuals.
Figure 6:
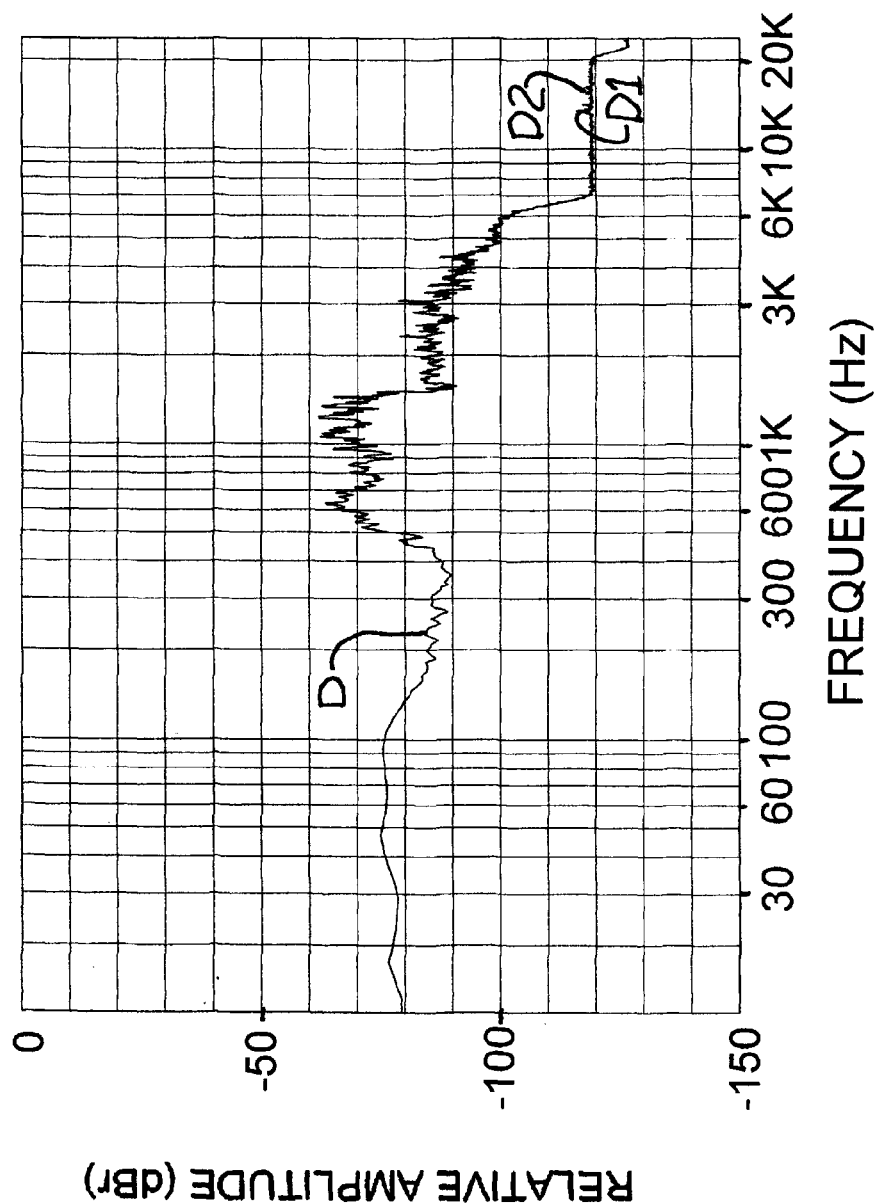
FIG. 6 is a graph showing the transmission of sound as a function of frequency in Hz when for a female patient with chronic back pain.
Figure 7:
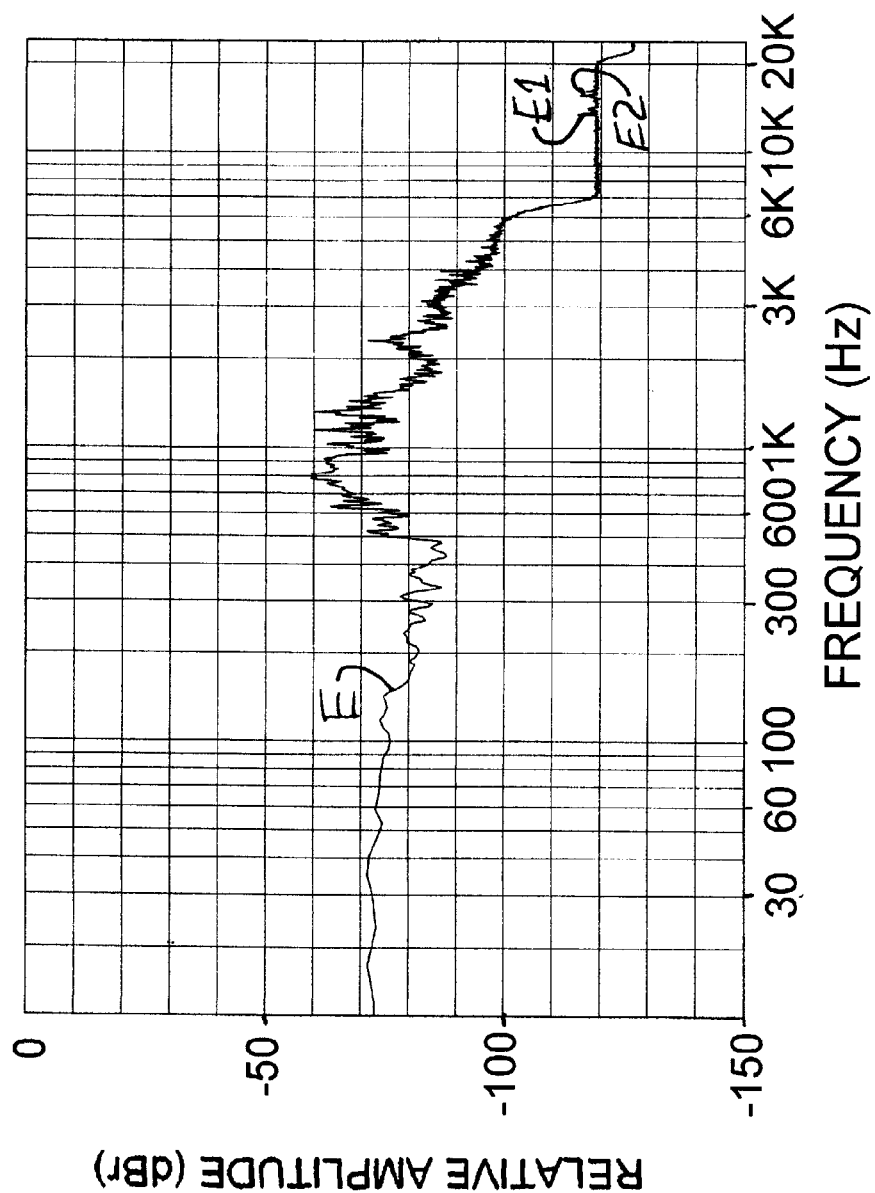
FIG. 7 is a graph showing the transmission of sound as a function of frequency in Hz when for a female patient with chronic neck and back pain.

FIG. 4, as is the case with FIGS. 5-7, provides a sound frequency axis on a logarithmic format which ranges generally between 20 Hz and 20 kHz. FIG. 4 provides the skilled reader with another view of the acoustic response in a normal test subject. In this example, speaker 16 and microphone unit 14 are placed in a sound isolated chamber to obtain a control trace A. To obtain test subject trace B, speaker 16 and microphone unit 14 are placed on a normal, asymptomatic test subject as sown in FIG. 1 and as described above. Note that contaminants 90 indicated in FIG. 1 are not present in a normal, asymptomatic test subject. Trace C is the difference between the control trace A and test subject trace B. As noted above, speaker 16 produces a spectrum of sounds ranging between 500 Hz and 1500 Hz. Microphone 14 records the frequency responses. As can be seen in trace B and trace C, two harmonic resonance zones are present between 10K Hz and 20K Hz. Although the scale in FIG. 4 is less conducive to close examination, the applicants believe that the two harmonic resonance zones are centered at approximately 14 kHz and 15.5 kHz and range roughly between 13.7 kHz and 14.25 kHz and roughly between 15.25 kHz and 15.75 kHz. The applicants believe that these harmonic resonance zones will be distorted in a characteristic manner in a subject who has abnormal, altered CSF as opposed to normal, unaltered CSF.

FIG. 5 provides a trace showing frequency response for three normal asymptomatic individuals. Subject A is a 50 year old male. Subject B is a 38 year old female and subject C is a 30 year old male. As can be seen in FIG. 5, the traces are almost exactly superimposed between 10K Hz and 20 KHz. However subject A, the 50 year old male, does show expanded resonance harmonic areas near 12K Hz and 17K Hz as indicated by the reference character "A" in those regions.

FIGS. 6 and 7 provide traces showing the sound transmission response for two female individuals having long term back pain or chronic neck and back pain. FIG. 6 presents a trace for subject D who had long term back pain when the data was gathered. FIG. 7 presents a trace for subject E who had long term neck and back pain when the data was gathered. In these cases, harmonic resonance zones D1, D2, E1 and E2 shown in FIGS. 6 and 7 are greatly reduced or suppressed from those of subjects A, B and C shown in FIG. 5. Because of these results, the applicants believe that it is possible to use sound transmission diagnosis apparatus 10 described above as shown in FIG. 1 to verify the presence of neck or back pain. The applicants have found that for patients complaining of long term or chronic neck and back pain, the resonance harmonic zones between 10k Hz and 20k Hz are typically markedly suppressed.

The applicants have described herein a new and useful apparatus and method for detecting the presence of pathogens in cerebrospinal fluid (CSF). This apparatus and method may be applied clinically to provide a non-invasive means to diagnose or rule out an infection which would cause the presence of pathogens or other disease state indicating contaminates in CSF. Such a non-invasive test facilitates the diagnoses or ruling out of meningitis without resorting to performing a risky and painful spinal tap procedure. This new non-invasive test will yield useful diagnostic data in a fraction of the time required to analyze CSF which might be of vital importance when there may not be a moment to lose. Moreover, such a non-invasive test may be conducted at a fraction of the cost of the traditional method described above, which is particularly advantageous at a time when medical costs are escalating beyond the reach of those who earn average incomes.

As noted above, it might be possible to use the apparatus described above to distinguish between ischemic and hemorrhagic strokes for patients who present stroke symptoms. If the present apparatus were to be widely distributed, it might become possible for patients during routine physical exams to have CNS and CSF resonance/harmonic data recorded and stored as medical data for the patient in a secure but accessible on-line source. Collecting such a CNS and CSF resonance/harmonic data might be indicated for patients having family history of stoke or who have other risk factors for stroke. The apparatus software of the present invention could include process steps that would optionally enable emergency personnel (either first responders or emergency room medical personnel) to use the apparatus to acquire a patient's resonance/harmonic data from a secure on-line source. Optionally, it might be possible to store the patient's CNS and CSF resonance/harmonic data in a microchip which is worn by the patent. The apparatus software would further includes optional steps for comparing the CSF resonance profile data on file for the patient to the CNS and CSF resonance/harmonic data collected from a patient presenting stroke symptoms. This might further increase the level of certainty for distinguishing between an ischemic and a hemorrhagic stroke.

It is to be understood that while certain forms of this invention have been illustrated and described, it is not limited thereto, except in so far as such limitations are included in the following claims and allowable equivalents thereof.

Having thus described the invention, what is claimed as new and desired to be secured by Letters Patent is:

1. An apparatus for measuring the acoustic response of the volume occupied by the central nervous system of a human for a human test subject for the purpose of detecting or ruling out meningitis, comprising:
   (a) an electronic speaker capable of receiving electronic signals and generating corresponding sounds having frequencies at least between 100 Hz and 1500 Hz, the electronic speaker being adapted for placement upon the spinal column of a test subject,
   (b) an electronic microphone capable of receiving transmitted sounds in a range between 30 Hz and 20 kHz and converting such sounds into corresponding electrical signals, the electronic microphone being adapted for placement upon the spinal column of a test subject,
   (c) a general purpose electronic digital computer having software which is (i) able to control the generation of the sound by the electronic speaker by generating corresponding electronic signals and transmitting the corresponding electronic signals to the speaker and (ii) able to receive and analyze electronic signals corresponding to transmitted sounds from the electronic microphone between the frequencies of 30 Hz and 20k Hz, the software of the general purpose computer being able to interpret the electronic signals received from the electronic microphone and thereby interpret the amplitudes of the transmitted received sounds and providing a record of the amplitude of the transmitted sound in decibels as a function of sound frequency,
   (d) the electronic microphone and the electronic speaker being operatively connected to the general purpose computer such that it is possible to position the electronic speaker and the electronic microphone in a spaced apart relationship on the spinal column of a human being with one of the electronic speaker or the electronic microphone placed in the cervical vertebrae area and the other of the electronic microphone and the electronic speaker placed in the lumbar vertebrae area, such that when the electronic speaker and the electronic microphone are placed upon the spine of a human being in a spaced relationship and when sounds varying across a range of frequencies or a sound having a predetermined frequency and of a predetermined amplitude or a predetermined range of amplitudes are conveyed into the human spine by the electronic speaker, the electronic microphone detects, transduces and transmits corresponding electronic signals to the general purpose electronic digital computer, the signals corresponding to the sounds of varying frequencies and varying amplitudes received by the microphone so that the general purpose electronic digital computer is able to receive such electronic signals from the microphone and provide a resonant frequency (RF) profile for the cerebrospinal fluid (CSF) of the test subject, the general purpose computer and software also configured to determine an RF profile for the cerebrospinal fluid (CSF) of the test subject and compare the RF profile of the test subject with the RF profiles of previous meningitis infected test subjects to either indicate an increased likelihood of a meningitis infection of the cerebrospinal fluid (CSF) of the test subject or to rule out the likelihood of a meningitis infection of the cerebrospinal fluid (CSF) of the test subject.

2. The apparatus of claim 1, wherein;
the electronic speaker includes a sound insulating shroud surrounding the electronic speaker which is adapted for placement on a vertebral area.

3. The apparatus of claim 1, wherein;
the electronic microphone includes a sound insulating shroud surrounding the electronic speaker which is adapted for placement on a vertebral area.

4. The apparatus of claim 1, wherein;
the electronic speaker and the electronic microphone include sound insulating shrouds which surround the electronic speaker and the electronic microphone which are adapted for placement on vertebral areas.

* * * * *